US007171030B2

(12) United States Patent
Foran et al.

(10) Patent No.: US 7,171,030 B2
(45) Date of Patent: Jan. 30, 2007

(54) SYSTEMS FOR ANALYZING MICROTISSUE ARRAYS

(75) Inventors: David J. Foran, Short Hills, NJ (US); Wenjin Chen, Piscataway, NJ (US)

(73) Assignee: University of Medicine & Denistry of New Jersey, Newark, NJ (US)

( * ) Notice: Subject to any disclaimer, the term of this patent is extended or adjusted under 35 U.S.C. 154(b) by 900 days.

(21) Appl. No.: 10/358,935

(22) Filed: Feb. 5, 2003

(65) Prior Publication Data

US 2003/0118222 A1    Jun. 26, 2003

Related U.S. Application Data

(63) Continuation-in-part of application No. 10/072,470, filed on Feb. 5, 2002, now Pat. No. 7,079,673, and a continuation-in-part of application No. 09/998,359, filed on Nov. 29, 2001, now Pat. No. 7,027,633.

(60) Provisional application No. 60/250,239, filed on Nov. 30, 2000.

(51) Int. Cl.
*G06K 9/00* (2006.01)
(52) U.S. Cl. .................. 382/128; 382/133; 702/21; 435/41
(58) Field of Classification Search ........ 382/128–134, 382/151, 172, 284, 294; 435/6, 13, 64, 91.1; 345/169, 172; 235/476, 470; 702/19, 20, 702/21, 27; 709/213; 128/920
See application file for complete search history.

(56) References Cited

U.S. PATENT DOCUMENTS 4,513,438 A    4/1985   Graham et al.

(Continued)

FOREIGN PATENT DOCUMENTS

WO    WO 93/14600    7/1993

(Continued)

OTHER PUBLICATIONS

Baumann, I. et al. Image Analysis Detects Lineage-Specific Morphologic Markers in Leukemic Blast Cells. Am. J. Clin. Pathol. 105, 23-30 (Jan. 1996).

(Continued)

*Primary Examiner*—Jingge Wu
*Assistant Examiner*—Abolfazl Tabatabai
(74) *Attorney, Agent, or Firm*—Kenneth Watov; Watov & Kipnes, P.C.

(57) ABSTRACT

A tissue microarray imaging system autonomously images, analyzes, and stores data for samples in a tissue microarray. The system may include a tissue microarray, a robotic microscope, and an imaging workstation that executes software to automatically control operation of the microscope to capture images from the microarray and analyze image results. A low magnification may be used to register samples within the microarray and obtain coordinates for each tissue specimen. Progressively higher magnifications may be used to analyze images of each registered specimen. Where multiple dyes are used to stain specimens, color separation techniques may be applied to independently measure and analyze each staining intensity. Images and quantitative data from the images may then be stored in a relational database for subsequent review. The system may be local, or may be Web-based for distributed control and sharing of results.

21 Claims, 8 Drawing Sheets

U.S. PATENT DOCUMENTS

| | | | |
|---|---|---|---|
| 4,705,756 | A | 11/1987 | Spillert et al. |
| 5,016,283 | A | 5/1991 | Bacus et al. |
| 5,616,905 | A | 4/1997 | Sugiyama |
| 5,733,739 | A | 3/1998 | Zakim et al. |
| 5,793,969 | A | 8/1998 | Kamentsky et al. |
| 5,930,461 | A | 7/1999 | Bernstein et al. |
| 5,991,028 | A | 11/1999 | Cabib et al. |
| 6,007,996 | A | 12/1999 | McNamara et al. |
| 6,078,681 | A | 6/2000 | Silver |
| 6,103,466 | A | 8/2000 | Grobet et al. |
| 6,103,518 | A | 8/2000 | Leighton |
| 6,121,960 | A | 9/2000 | Carroll et al. |
| 6,148,096 | A | 11/2000 | Pressman et al. |
| 6,226,392 | B1 | 5/2001 | Bacus et al. |
| 6,272,235 | B1 | 8/2001 | Bacus et al. |
| 6,274,323 | B1 * | 8/2001 | Bruchez et al. ................ 435/6 |
| 6,633,659 | B1 * | 10/2003 | Zhou .......................... 382/129 |
| 6,658,287 | B1 | 12/2003 | Litt et al. |
| 6,692,916 | B2 | 2/2004 | Bevilacqua et al. |
| 6,711,283 | B1 * | 3/2004 | Soenksen ................... 382/133 |

FOREIGN PATENT DOCUMENTS

| | | |
|---|---|---|
| WO | WO 96/07161 | 3/1996 |
| WO | WO 99/30264 | 6/1999 |
| WO | WO 99/44063 | 9/1999 |

OTHER PUBLICATIONS

Bennett, J.M., et al., "Proposals for the Classification of the Acute Leukaemias", Br. J. Haematol., vol. 33, pp. 451-458 (1976).

Cabral, J.E. Jr. & Kim, Y. Multimedia Systems for Telemedicine and Their Communications Requirements. *IEEE Communications Magazine* 34, 20-27 (Jul. 1, 1996).

Chan, J. K. C., et al., "A Revised European-American Classification of Lymphoid Neoplasms Proposed by the International Lymphoma Study Group," Amer. J. Clin. Pathol., vol. 103:(5), pp. 543-560 (1995).

Comaniciu, D. and Meer, P., "Distribution Free Decomposition of Multivariate Data," Pattern Anal. Applicat, vol. 2, pp. 22-30 (1999).

Dryden, I.L., and Mardia, K.V., Statistical Shape Analysis, West Sussex, U.K.: Wiley, pp. 251-278 (1998).

Garcia-Conde, J. and Cabanillas, F., "Mantle Cell Lymphoma: A Lymphoproliferative Disorder Associate with Aberrant Function of the Cell Cycle," Leukemia, vol. 10:(S2), pp. S78-S83 (1996).

Geisler, C. H., et al., "Prognostic Importance of Flow Cytomeric Immunophenotyping of 540 Consecutive Patients with B-Cell Chronic Lymphocytic Leukemia," Blood, vol. 78:(7), pp. 1795-1802 (1991).

Genesereth M., and Nilson, N., Logical Foundations of Artificial Intelligence, Palo Alto, CA: Morgan Kaufman,, pp. 19-45 (1988).

Grimes, G.J., "Remote Microscopy for Hi-Res Real-Time interactive pathology," Advanced Imaging., vol. 12:7, pp. 12-16 (1998).

Groshong, B.R. Estimating Simple Closed Contours in Images. *Proc. Ann. Symposium Comp. Based Med. Systems* 5, 35-43 (Jun. 14, 1992).

Harms, H., et al., "Segmentation of Stained Blood Cell Images Measured at High Scanning Density with High Magnification and High Numerical Aperture Optics," Cytometry, vol. 7, pp. 522-531 (1986).

Head, D. R., et al., "Reproducibility of the French-American-British Classification of Acute Leukemia: The Southwest Oncology Group Experience," Amer. J. Hematol., vol. 18, pp. 47-57 (1985).

Hu, M. K, et al., "Visual Pattern Recognition by Moment Invariants," IRE Trans, Inform. Theory Inform. Technol., vol. 8, pp. 179-187 (1962).

Kauppinen, H., et al., "An Experimental Comparison of Autoregressive and Fourier-Based Descriptors in 2D Shape Classification," IEEE Trans. Pattern Anal. Machine Intell., vol. 17(2), pp. 201-207 (1995).

Kendall, D.G., "A Survey of the Statistical Theory of Shape," Statistical Science, vol. 4(2), pp. 87-120 (1989).

Khotanzad, A., and Hong, Y. H., "Invariant Image Recognition by Zernike Moments," IEEE Trans. Pattern Anal. Machine Intell., vol. 12(5), pp. 489-497 (1990).

Khotanzad, A , and Hong, Y. H., "Rotation Invariant Image Recognition Using Features Selected Via a Systematic Method", Pattern Recognit., vol. 23:10, pp. 1089-1101 (1990).

Kilo, M. N., and Dorfman, D. M., "The Utility of Flow Cytometric Immunophenotypic Analysis in the Distinction of Small Lymphocytic Lymphoma/Chronic Lymphocytic Leukemia from Mantle Cell Lymphoma," Amer. J. Clin. Pathol., vol. 105, pp. 451-457 (1996).

Kuhl, F., P and Giardina, C.R., "Elliptic Fourier Features of a Closed Contour," Computer Graph. Image Process., vol. 18, pp. 236-258 (1982).

Mao, J. and Jain, A.K., "Texture Classification Segmentation Using Multiresolution Simultaneous Autoregressive Models," Pattern Recognit., vol. 25(2), pp. 173-188 (1992).

Rozman, C., and Montserrat, E., "Chronic Lymphocytic Leukemia", N.E.J.M., vol. 333:(16), pp. 1052-1057 (1995).

Vadlamudi, G., et al., "Leukemic Phase of Mantle Cell Lymphoma Two Case Reports and Review of the Literature", Arch. Pathol. Lab. Med., vol. 120, pp. 35-40 (1996).

Yatabe, Y, et al., "Clinicopathologic Study of PRAD1/Cyclin D1 Overexpressing Lymphoma with Special Reference to Mantle Lymphoma", Amer. J. Surg. Pathol., vol. 20:(9), pp. 1110-1122 (1996).

Zink, S., and Jaffe, C. C., "Medical Imaging Databases, A National Institutes of Health Workshop," Investigative Radiol., vol. 28:(4), pp. 366-372 (1993).

* cited by examiner

SYSTEMS FOR ANALYZING MICROTISSUE ARRAYS

RELATED APPLICATIONS

This application is a continuation-in-part of U.S. patent application Ser. No. 10/072,470, filed on Feb. 5, 2002, now U.S. Pat. No. 7,079,673, and a continuation-in-part of U.S. patent application Ser. No. 09/998,359 filed on Nov. 29, 2001, now U.S. Pat. No. 7,079,633, which claims the benefit of U.S. Prov. App. No. 60/250,239, filed on Nov. 30, 2000. The entire teachings of these references are incorporated herein by reference.

GOVERNMENT INTERESTS

The United States Government may have rights in this invention pursuant to National Institute of Health contract 1 RO1 LM007455-01A1 from the National Library of Medicine, and National Science Foundation grants IRI-9530546 and IRI-9618854.

BACKGROUND OF THE INVENTION

Tissue microarrays are a method of harvesting small discs of tissue from a range of standard histologic sections and arranging them on a recipient paraffin block such that hundreds or thousands of discs can be analyzed simultaneously. This technique allows maximization of tissue resources by analysis of small core biopsies of blocks, rather than complete sections. A carefully planned array of tissues can be constructed with cases from pathology tissue block archives, such that a 20-year survival analysis can be performed on a cohort of 600 or more patients by use of only a few microliters of antibody.

Tissue microarray technology has numerous advantages in addition to tissue amplification. For example, each specimen is treated in an identical manner. Like conventional formalin-fixed paraffin embedded material, tissue microarrays are amenable to a wide variety of techniques, including histochemical stains, immunologic stains with either chromogenic or fluorescent visualization, in situ hybridization (including messenger RNA in situ hybridization and fluorescence in situ hybridization) and even microdissection techniques. For each of these protocols conventional sections can have substantial slide-to-slide variability associated with processing 300 slides (e.g. 20 batches of 15 slides). By contrast, the tissue microarrays allow an entire cohort to be analyzed on a single slide. Thus, reagent concentrations are identical for each case, as are incubation times and temperatures and wash conditions. Antigen retrieval can be another significant variable in conventional sections, which is mitigated by the identical treatment of specimens in a microarray. As a further advantage, only a few microliters of reagent may be required to analyze an entire cohort in a microarray. This advantage raises the possibility of using tissue microarrays in certain screening procedures, such as hybridoma screening, where the protocol is not amenable to the use of conventional sections.

Currently, the primary method used to evaluate microarrays involves manual review of hundreds of tissue microarray ("TMA") cores under a microscope, while subjectively evaluating and scoring the signal at each location. An alternate, but less utilized approach is to sequentially digitize specimens for subsequent assessment. Both procedures involve manually and systematically reviewing the TMA sample under the microscope, which is a slow, tedious process, and which is especially error-prone because it is easy to loose track of a current array while navigating among the regularly arranged specimens. This is especially true at higher (e.g. 20×) magnifications.

Tissue microarrays also present some special problems such as heterogeneity of tissue sections, sub-cellular localization of staining, and background signal. Depending on the type of tumor or tissue section analyzed, the area of interest may represent nearly the entire disc or only a small percentage thereof. For example, a pancreatic carcinoma or lobular carcinoma of the breast with substantial desmoplastic response may show stromal tissue representing a large percentage of the total area of the disc. If the goal of the assay is to determine epithelial cell expression of a given marker, a protocol must be used that evaluates only that region of the disc. The protocol must not only be able to select the region of interest but also normalize it so that the expression level read from any given disc can be compared with that of other discs. Sub-cellular localization presents a host of additional challenges when comparing nuclear or membranous stainings which are quite different from those in total cytoplasmic staining.

There remains a need for a systematic approach to collecting, analyzing, and storing data from tissue microarrays.

SUMMARY OF THE INVENTION

A tissue microarray imaging system autonomously images, analyzes, and stores data for samples in a tissue microarray. The system may include a tissue microarray, a robotic microscope, and an imaging workstation that executes software to automatically control operation of the microscope to capture images from the microarray and analyze image results. A low magnification may be used to register samples within the microarray and obtain coordinates for each tissue specimen. Progressively higher magnifications may be used to analyze images of each registered specimen. Where multiple dyes are used to stain specimens, color separation techniques may be applied to independently measure and analyze each staining intensity. Images and quantitative data from the images may then be stored in a relational database for subsequent review. The system may be local, or may be Web-based for distributed control and sharing of results.

BRIEF DESCRIPTION OF DRAWINGS

The foregoing and other objects and advantages of the invention will be appreciated more fully from the following further description thereof, with reference to the accompanying drawings, wherein.

DETAILED DESCRIPTION OF CERTAIN EMBODIMENTS OF THE INVENTION

To provide an overall understanding of the invention, certain illustrative embodiments will now be described, including a system for automated analysis of a tissue microarray. However, it will be understood that the methods and systems described herein can be suitably adapted to any environment where a number of approximately regularly spaced specimens are to be visually inspected in some systematic fashion. For example, the systems and methods are applicable to a wide range of biological specimen images, and in particular to analysis or diagnosis involving cellular, or other microscopic, visual data. These and other applications of the systems described herein are intended to fall within the scope of the invention.

Figure 1:
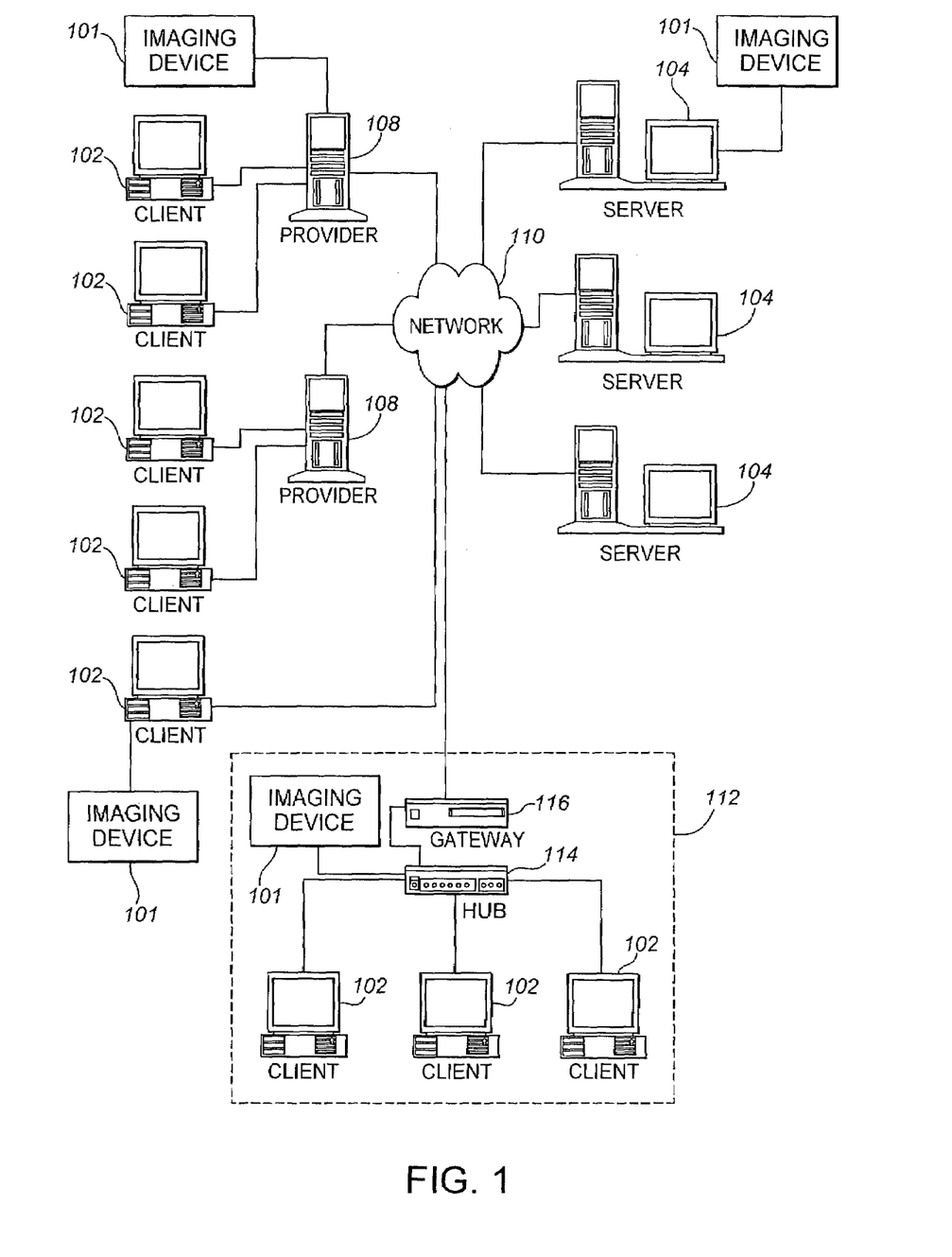
FIG. 1 shows a schematic diagram of the entities involved in an embodiment of a method and system disclosed herein.

FIG. 1 shows a schematic diagram of the entities involved in an embodiment of a method and system disclosed herein. In a system 100, one or more imaging devices 101, a plurality of clients 102, servers 104, and providers 108 are connected via an internetwork 110. It should be understood that any number of clients 102, servers 104, and providers 108 could participate in such a system 100. The system may further include one or more local area networks ("LAN") 112 interconnecting clients 102 through a hub 114 (in, for example, a peer network such as Ethernet) or a local area network server 114 (in, for example, a client-server network). The LAN 112 may be connected to the internetwork 110 through a gateway 116, which provides security to the LAN 112 and ensures operating compatibility between the LAN 112 and the internetwork 110. Any data network may be used as the internetwork 110 and the LAN 112.

In one embodiment, the internetwork 110 is the Internet, and the World Wide Web provides a system for interconnecting imaging devices 101, clients 102 and servers 104 through the Internet 110. The internetwork 110 may include a cable network, a wireless network, and any other networks for interconnecting clients, servers and other devices.

As depicted, one of the imaging devices 101 may be connected to one of the clients 102, one of the servers 104, the hub 114 of the LAN 112, or directly to one of the providers 108, and may include suitable hardware and software for connecting to the internetwork 110 through any of the above devices or systems. One of the imaging devices 101 that may be used in the systems herein is a robotic microscope, such as an Olympus AX70 equipped with a Prior 6-way robotic stage and motorized turret (available from Prior Scientific, Inc.) coupled to an Olympus DC330 720-line, 3-chip video camera and a Flashpoint 128 high-resolution frame grabber (available from Integral Technologies, Inc.) high-resolution color video camera. This imaging device 101 may be used to gather images for the image database, as described in more detail below. More generally, the imaging devices 101 may be any robotic microscope or other device allowing electronic control over a specimen stage, a light level, an objective lens, and a focus, as well as parameters of digitization such as rate and resolution. The imaging devices 101 may be steered to an x-position and a y-position of a specimen through electronic control. Still more generally, the term 'imaging device' as used herein should be understood to include cameras, microscopes, or any other device for capturing and/or providing an image in electronic form, and should further be understood to include to include a mass storage device or other device for providing a previously captured electronic image.

In the systems described herein, the imaging devices 101 are used to obtain images of tissue microarrays. A tissue microarray may be a block of paraffin or similar material having holes placed therein to receive tissue samples. The samples placed in the tissue microarray are typically placed in some regular pattern, such as a rectangular matrix of cores, possibly with rows and/or columns skipped at regular intervals to facilitate visual navigation of the array. In such an embodiment, each core has an x-coordinate and a y-coordinate at or near the center of the core, which may be identified and used to locate the core as described below. Other regular or irregular patterns may also, or instead be used, provided each core can be located and revisited within the array.

It will be appreciated that, while discs are a common geometry used for samples in a tissue microarray, other geometries are possible, including regular and irregular geometric profiles, and may be used with the system described herein, provided they are amenable to punching of matching shapes in a tissue source (for taking samples) and the receiving material (e.g., paraffin). The terms 'disc' or 'core', as used herein, are intended to include any such geometry. The terms 'specimen' or 'biological specimen' are intended to refer to any biological (or inert control) material that may be sampled and inserted into a tissue microarray.

An exemplary client 102 includes the conventional components of a client system, such as a processor, a memory (e.g. RAM), a bus which couples the processor and the memory, a mass storage device (e.g. a magnetic hard disc or an optical storage disc) coupled to the processor and the memory through an I/O controller, and a network interface coupled to the processor and the memory, such as modem, digital subscriber line ("DSL") card, cable modem, network interface card, wireless network card, or other interface device capable of wired, fiber optic, or wireless data communications. One example of such a client 102 is a personal computer equipped with an operating system such as Microsoft Windows 2000, Microsoft Windows NT, Unix, Linux, and Linux variants, along with software support for Internet communication protocols. The personal computer may also include a browser program, such as Microsoft Internet Explorer or Netscape Navigator, to provide a user interface for access to the Internet 110. Although the personal computer is a typical client 102, the client 102 may also be a workstation, mobile computer, Web phone, television set-top box, interactive kiosk, personal digital assistant, or other device capable of communicating over the Internet 110. As used herein, the term "client" is intended to refer to any of the above-described clients 102, as well as proprietary network clients designed specifically for the systems described herein, and the term "browser" is intended to refer to any of the above browser programs or other software or firmware providing a user interface for navigating the Internet 110 and/or communicating with the medical image processing systems.

An exemplary server 104 includes a processor, a memory (e.g. RAM), a bus which couples the processor and the memory, a mass storage device (e.g. a magnetic or optical disc) coupled to the processor and the memory through an I/O controller, and a network interface coupled to the processor and the memory. Servers may be organized as layers of clusters in order to handle more client traffic, and may include separate servers for different functions such as a database server, a file server, an application server, and a Web presentation server. Such servers may further include one or more mass storage devices such as a disc farm or a redundant array of independent disc ("RAID") system for additional storage and data integrity. Read-only devices, such as compact disc drives and digital versatile disc drives, may also be connected to the servers. Suitable servers and mass storage devices are manufactured by, for example, Compaq, IBM, and Sun Microsystems. As used herein, the term "server" is intended to refer to any of the above-described servers 104.

Focusing now on the internetwork 110, one embodiment is the Internet. The structure of the Internet 110 is well known to those of ordinary skill in the art. However, one may practice the present invention on a wide variety of other communication networks, including interactive television networks, telephone networks, wireless data transmission systems, two-way cable systems, customized computer networks, interactive kiosk networks, or ad hoc packet relay networks. One embodiment of the internetwork 110 includes Internet service providers 108 offering dial-in service, such as Microsoft Network, America OnLine, Prodigy and CompuServe. It will be appreciated that the Internet service providers 108 may also include any computer system which can provide Internet access to a client 102. Of course, the Internet service providers 108 are optional, and in some cases, the clients 102 may have direct access to the Internet 110 through a dedicated DSL service, ISDN leased lines, T1 lines, digital satellite service, cable modem service, or any other high-speed connection to a network point-of-presence. Any of these high-speed services may also be offered through one of the Internet service providers 108.

In its present deployment as the Internet, the internetwork 110 consists of a worldwide computer network that communicates using protocols such as the well-defined Transmission Control Protocol ("TCP") and Internet Protocol ("IP") to provide transport and network services. It will be appreciated that other internetworks 110 may be used with the invention instead of, or in addition to, the Internet. For example, the internetwork 110 may be a wide-area network, a local-area network, or corporate-area network.

In an exemplary embodiment, a browser, executing on one of the clients 102, retrieves a Web document at an address from one of the servers 104 via the internetwork 110, and displays the Web document on a viewing device, e.g., a screen. A user can retrieve and view the Web document by entering, or selecting a link to, a URL in the browser. The browser then sends an http request to the server 104 that has the Web document associated with the URL. The server 104 responds to the http request by sending the requested Web document to the client 102. The Web document is an http object that includes plain text, or ASCII, conforming to the HyperText Markup Language ("HTML"). Other markup languages are known and may be used on appropriately enabled browsers and servers, including the Dynamic HyperText Markup Language ("DHTML"), the Extensible Markup Language ("XML"), the Extensible Hypertext Markup Language ("XHTML"), and the Standard Generalized Markup Language ("SGML").

Each Web document may contain hyperlinks to other Web documents. The browser displays the Web document on the screen for the user and the hyperlinks to other Web documents are emphasized in some fashion such that the user can identify and select each hyperlink. To enhance functionality, a server 104 may execute programs associated with Web documents using programming or scripting languages, such as Perl, C, C++, or Java. A server 104 may also use server-side scripting languages such as ColdFusion from Allaire, Inc., or PHP. These programs and languages perform "back-end" functions such as transaction processing, database management, content searching, and implementation of application logic for applications. A Web document may also include references to small client-side applications, or applets, that are transferred from the server 104 to the client 102 along with a Web document and executed locally by the client 102. Java is one popular example of a programming language used for applets. The text within a Web document may further include (non-displayed) scripts that are executable by an appropriately enabled browser, using a scripting language such as JavaScript or Visual Basic Script. Browsers may further be enhanced with a variety of helper applications to interpret various media including still image formats such as JPEG and GIF, document formats such as PS and PDF, motion picture formats such as AVI and MPEG, and sound formats such as MP3 and MIDI. These media formats, along with a growing variety of proprietary media formats, may be used to enrich a user's interactive and audio-visual experience as each Web document is presented through the browser. The term "page" as used herein is intended to refer to the Web document described above, as well as any of the above-described functional or multimedia content associated with the Web document.

Figure 2:
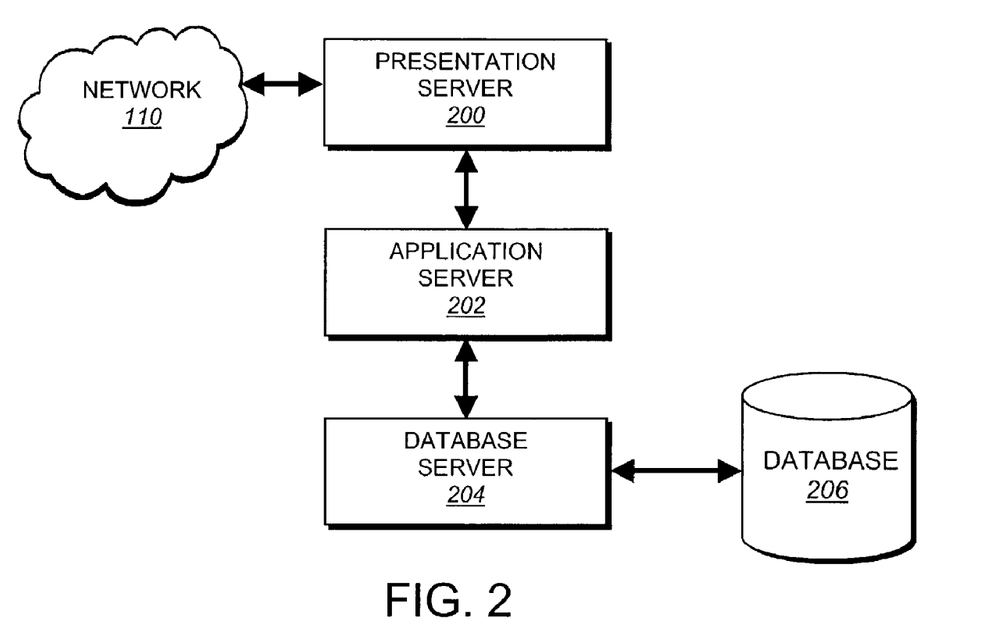
FIG. 2 shows a block diagram of a server that may be used with the systems described herein.

FIG. 2 shows a block diagram of a server that may be used with the systems described herein. In this embodiment, the server 104 includes a presentation server 200, an application server 202, and a database server 204. The application server 202 is connected to the presentation server 200. The database server 204 is also connected to the presentation server 200 and the application server 202, and is further connected to a database 206 embodied on a mass storage device. The presentation server 200 includes a connection to the internetwork 110. It will be appreciated that each of the servers may comprise more than one physical server, as required for capacity and redundancy, and it will be further appreciated that in some embodiments more than one of the above servers may be logical servers residing on the same physical device. One or more of the servers may be at a remote location, and may communicate with the presentation server 200 through a local area or wide area network. The term "host," as used herein, is intended to refer to any combination of servers described above that include a presentation server 200 for providing access to pages by the clients 102. The term "site," as used herein, is intended to refer to a collection of pages sharing a common domain name address, or dynamically generated by a common host, or accessible through a common host (i.e., a particular page may be maintained on or generated by a second, remote or local server, but nonetheless be within a 'site').

The presentation server 200 provides an interface for one or more connections to the internetwork 110, thus permitting more than one of the clients 102 (FIG. 1) to access the site at the same time. In one embodiment, the presentation server 200 comprises a plurality of enterprise servers, such as the ProLiant Cluster available from Compaq Computer Corp., or a cluster of E250's from Sun MicroSystems running Solaris 2.7. Other suitable servers are known in the art and are and may be adapted to use with the systems described herein, such as, for example, an iPlanet Enterprise Server 4.0 from the Sun/Netscape Alliance. The presentation server 200 may also use, for example, Microsoft's .NET technology, or use a Microsoft Windows operating system, with a "front end" written in Microsoft Active Server Page ("ASP"), or some other programming language or server software capable of integrating ActiveX controls, forms, Visual Basic Scripts, JavaScript, Macromedia Flash Technology multimedia, e-mail, and other functional and multimedia aspects of a page. Typically, the front end includes all text, graphics, and interactive objects within a page, along with templates used for dynamic page creation. The presentation server 200 maintains one or more connections to the Internet 110. Where there is substantial network traffic, the connections are preferably provided by a tier one provider, i.e., one of the dozen or so national/international Internet backbones with cross-national links of T3 speeds or higher, such as MCI, UUNet, BBN Planet, and Digex.

A client 102 (FIG. 1) accessing an address hosted by the presentation server 200 will receive a page from the presentation server 200 containing text, forms, scripts, active objects, hyperlinks, etc., which may be collectively viewed using a browser. Each page may consist of static content, i.e., an HTML text file and associated objects (*.avi, *.jpg, *.gif, etc.) stored on the presentation server, and may include active content including applets, scripts, and objects such as check boxes, drop-down lists, and the like. A page may be dynamically created in response to a particular client 102 request, including appropriate queries to the database server 204 for particular types of data to be included in a responsive page. It will be appreciated that accessing a Web page is more complex in practice, and includes, for example, a DNS request from the client 102 to a DNS server, receipt of an IP address by the client 102, formation of a TCP connection with a port at the indicated IP address, transmission of a GET command to the presentation server 200, dynamic page generation (if required), transmission of an HTML object, fetching additional objects referenced by the HTML object, and so forth.

The application server 202 provides the "back-end" functionality of the Web site, and includes connections to the presentation server 200 and the database server 204. In one embodiment, the presentation server 200 comprises an enterprise server, such as one available from Compaq Computer Corp., running the Microsoft Windows NT operating system, or a cluster of E250's from Sun MicroSystems running Solaris 2.7. The back-end software may be implemented using pre-configured e-commerce software, such as that available from Pandesic, to provide back-end functionality including transaction processing, billing, data management, financial transactions, order fulfillment, and the like. The application server 202 may include a software interface to the database server 204, as well as a software interface to the front end provided by the presentation server 200. The application server 200 may also use a Sun/Netscape Alliance Server 4.0.

The database server 204 may be an enterprise server, such as one available from Compaq Computer Corp., running the Microsoft Windows NT operating system or a cluster of E250's from Sun MicroSystems running Solaris 2.7, along with software components for database management. Suitable databases are provided by, for example, Oracle and Sybase. The database server 204 may also include one or more databases 206, typically embodied in a mass-storage device. The databases 206 may include, for example, user interfaces, search results, search query structures, lexicons, user information, and the templates used by the presentation server to dynamically generate pages. It will be appreciated that the databases 206 may also include structured or unstructured data, as well as storage space, for use by the presentation server 200 and the application server 202. In operation, the database management software running on the database server 204 receives properly formatted requests from the presentation server 200, or the application server 202. In response, the database management software reads data from, or writes data to, the databases 206, and generates responsive messages to the requesting server. The database server 204 may also include a File Transfer Protocol ("FTP") or a Secure Shell ("SSH") server for providing downloadable files.

While the three tier architecture described above is one conventional architecture that may be used with the systems described herein, it will be appreciated that other architectures for providing data and processing through a network are known and may be used in addition to, or in conjunction with, or in place of the described architecture. Any such system may be used, provided that it can support aspects of the image processing system described herein.

Computers such as the client 102 or the server 104 may be coupled to an imaging device 101 to control operation of the imaging device 101 and to provide an interface to the Internet for sharing image data and control information such that one of the imaging devices 101 may share images with, or be controlled by, any other client 102 connected to the internetwork 110.

Figure 3:
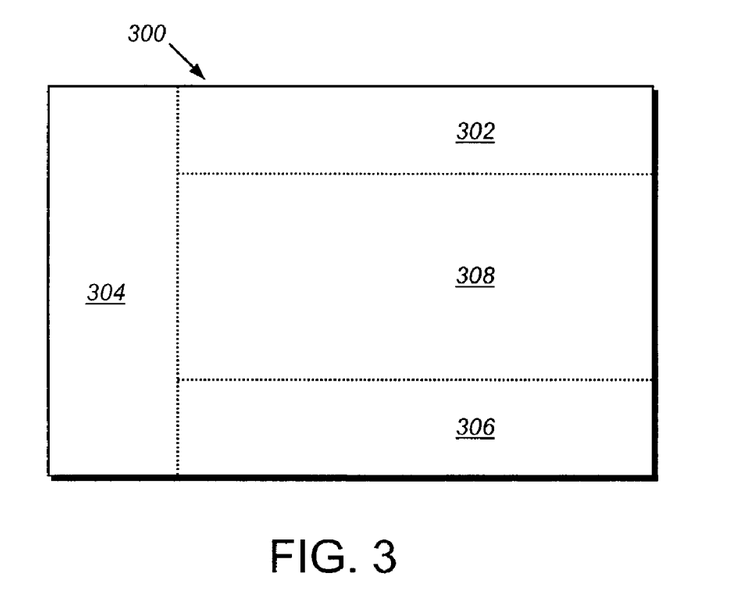
FIG. 3 shows a page that may be used as a user interface.

FIG. 3 shows a page that may be used as a user interface. The page 300 may include a header 302, a sidebar 304, a footer 306 and a main section 308, all of which may be displayed at a client 102 using a browser. The header 302 may include, for example, one or more banner advertisements and a title of the page. The sidebar 304 may include a menu of choices for a user at the client 102. The footer 306 may include another banner advertisement, and/or information concerning the site such as a "help" or "webmaster" contact, copyright information, disclaimers, a privacy statement, etc. The main section 308 may include content for viewing by the user. The main section 308 may also include, for example, tools for electronically mailing the page to an electronic mail ("e-mail") account, searching content at the site, and so forth. It will be appreciated that the description above is generic, and may be varied according to where a client 102 is within a Web site related to the page, as well as according to any available information about the client 102 (such as display size, media capabilities, etc.) or the user.

A Web site including the page 300 may use cookies to track users and user information. In particular, a client 102 accessing the site may be accessed to detect whether the client 102 has previously accessed the page or the site. If the client 102 has accessed the site, then some predetermined content may be presented to the client 102. If the client 102 does not include a cookie indicating that the client 102 has visited the site, then the client 102 may be directed to a registration page where information may be gathered to create a user profile. The client 102 may also be presented with a login page, so that a pre-existing user on a new client 102 may nonetheless bypass the registration page.

The site may provide other functionality to the client 102. For example, the site may provide a search tool by which the client 102 may search for content within the site, or content external to the site but accessible through the internetwork 110. As another example, the site may display local or remote news items and stories that are topical to the site. The site may provide an interface for structured queries to, browsing of, and review of images and data in, the database that stores archived tissue microarrays. Tools may also be provided for other network functions associated with the system, such as remotely initiating data capture for a tissue microarray, manual control of a robotic microscope or other imaging device used to obtain tissue microarray images, or manual control of an imaging device.

The interface may be embodied in any software and/or hardware client operating on a client device, including a browser along with any suitable plug-ins, a Java applet, a Java application, a C or C++ application, or any other application or group of applications operating on a client device. In one embodiment, the user interface may be deployed through a Web browser. In one embodiment, the user interface may be deployed as an application running on a client device, with suitable software and/or hardware for access to an internetwork. In these and other embodiments, certain image processing functions, as well as database storage and management functions, may be distributed in any suitable manner between a client device, one or more imaging devices, and one or more servers.

It will be appreciated that a number of enhancements may be provided to the user interface. For example, voice-activated commands may be provided. Voice communication between the user and computer may enable a user to navigate among digital archives of tissue microarrays or to direct the inspection of disc specimens, or "cores", while they are viewed with the robotic microscope. Valid voice commands may include, for example, "next core", "current core", "previous core", and "where am I?". The user can also direct the scope to move to a specific core location by indicating its row and column. For quality control purposes the system may support programmed screening of samples, in which each core in an array is retrieved and displayed to the user. Browsing through cores may also be permitted, such as with a raster or snake pattern through the tissue microarray. A random mode may also be provided, in which the system randomly presents cores to user.

Figure 4:
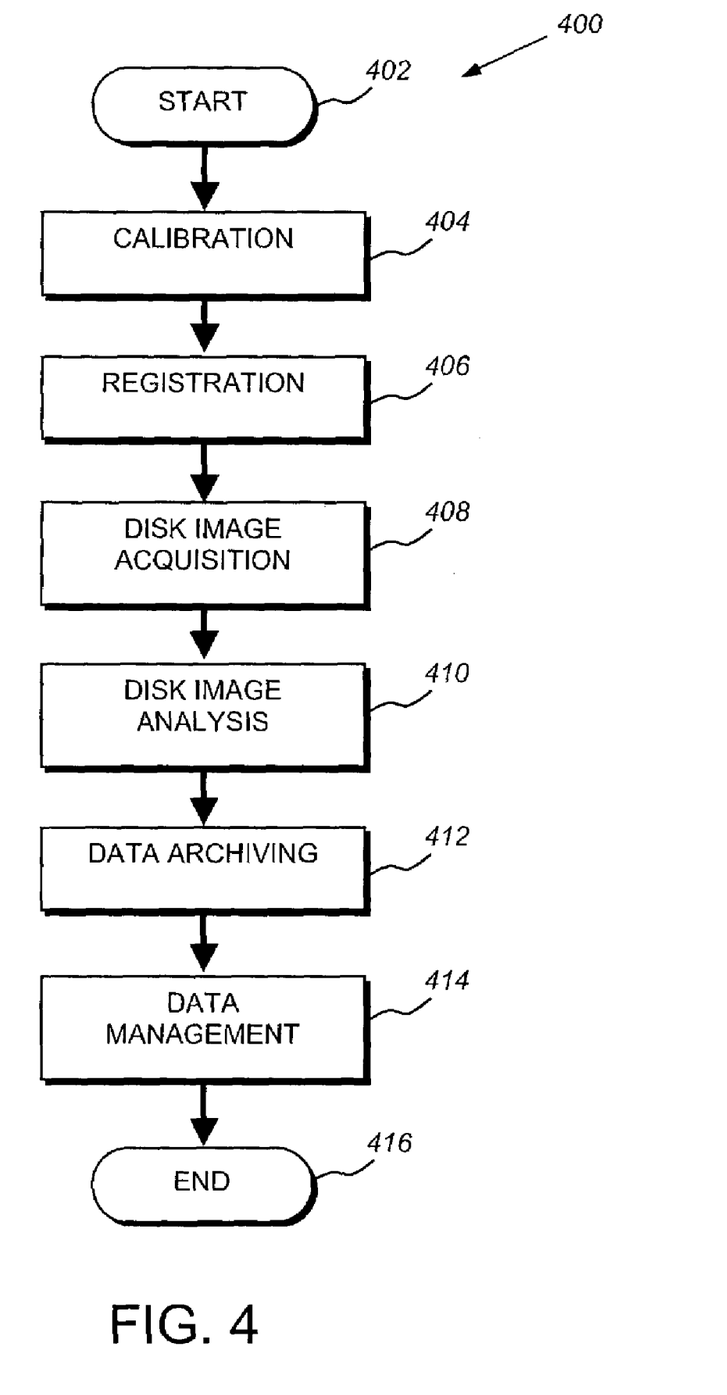
FIG. 4 is a flow chart of a process for capturing, processing, and storing images of discs in a tissue microarray.

FIG. 4 is a flow chart of a process for capturing, processing, and storing images of discs in a tissue microarray. As noted in the discussion above, discs are a common geometry used for tissue microarrays. However, other geometries are possible, including regular and irregular geometric profiles, and may be used with the system described herein, provided they are amenable to punching of matching shapes in a tissue source (for taking samples) and a block of paraffin or similar material (for receiving the samples). The terms 'disc' or 'core', as used herein, are intended to include any such geometry. The terms 'specimen' or 'biological specimen' are intended to refer to any biological (or inert control) material that may be sampled and inserted into a tissue microarray.

The process 400 may be realized in hardware, software, or some combination of these. The process 400 may be realized in one or more microprocessors, microcontrollers, embedded microcontrollers, programmable digital signal processors or other programmable device, along with internal and/or external memory such as read-only memory, programmable read-only memory, electronically erasable programmable read-only memory, random access memory, dynamic random access memory, double data rate random access memory, Rambus direct random access memory, flash memory, or any other volatile or non-volatile memory for storing program instructions, program data, and program output or other intermediate or final results. The process 400 may also, or instead, include an application specific integrated circuit, a programmable gate array, programmable array logic, or any other device that may be configured to process electronic signals.

Any combination of the above circuits and components, whether packaged discretely, as a chip, as a chipset, or as a die, may be suitably adapted to use with the systems described herein. It will further be appreciated that the below process 400 may be realized as computer executable code created using a structured programming language such as C, an object-oriented programming language such as C++ or Java, or any other high-level or low-level programming language that may be compiled or interpreted to run on one of the above devices, as well as heterogeneous combinations of processors, processor architectures, or combinations of different hardware and software. The process 400 may be deployed using software technologies or development environments including a mix of software languages, such as Microsoft IIS, Active Server Pages, Java, C++, Oracle databases, SQL, and so forth.

The process 400 starts 402 with a calibration of the tissue microarray image, as shown in step 404. A user interface may be provided to assist with the calibration, which may depend on the particular specimen under study and the particular microscope being used. For example, color may be calibrated to accommodate measurement of protein expression for a full spectrum of stains and biologic targets (e.g. stromal, epithelial cells). In this example, the system may perform a mapping of one or more red, green, and blue intensity values of an imaged microarray into $L^*u^*v^*$ color space and then, using polar coordinates, plot the mapped values into an graphical window equipped with interactive controls while a crude multidimensional segmentation of the digitized microarray is performed. Using the graphical controls a user may interactively refine the segmentation by sketching lines of demarcation between clusters within the polar plot while a continuously updated output image shows the effect of utilizing the new parameters. Once the user is satisfied with the segmentation for one disc, the calibration may be applied to the remaining discs on the microarray. These and other known calibration techniques may be used to normalize image data across a number of different tissue microarrays.

Once the system is calibrated, the discs in the tissue microarray may be registered, as shown in step 406. The rows and columns of discs in the microarray are rarely straight, and slight distortions to each disc are typically introduced during specimen preparation. To account for this, the system may register each disc to ensure accurate stage localization. Slight errors in lens co-focal and co-centering may be compensated for using empirical data. A more detailed description of a technique for registration of image content in a tissue microarray is described in further detail below.

Once discs have been located, the process 400 may commence disc image acquisition, as shown in step 408. Using the location data obtained above, the imaging device may be automatically directed to acquire an image of each disc at a higher magnification. The process 400 may auto-focus and background-correct each disc when the image is captured. Auto-focusing may be, for example, through entropy minimization. In order to enhance image detail, the imaging device may capture images of subsections of a disc at higher magnification, which may then be combined to form a single, high-detail image. It will be appreciated that the terms "capture", "acquire", and similar terms, as used with respect to digital images as described herein, may refer to capture of an entire frame of digital image data, or to retrieval of a portion of an entire frame of digital data, or to the creation of a composite digital image formed from more than one entire frame of digital data, or any combination of these. As such, unless otherwise specifically indicated, the terms "capture", "acquire" and similar terms should be understood to mean any retrieval of identified subject matter, or a field of view at an identified location, as obtained through a digital camera, from a database, or some processed form of either or both of these.

After each disc image has been acquired, the images may be analyzed, as shown in step 410. This may be any quantitative or other objective analysis that may be realized in computer software. The images may be processed, for example, into their constituent visual components (e.g. Stromal, epithelial cell regions). The system may then produce measures to determine the signal strength for protein expression (intensity) per unit area and also in terms of integrated density of protein expression. Additionally, measures for multi-resolution texture and morphometric measurements may be generated, as well as any other useful quantitative measure that may be derived from the images, including measures of shape, size, color, color gradient, contrast, and so forth.

It will be appreciated that different analysis techniques may be used according to the diagnostic significant of specimens under study. For example, depending on the type of tumor or tissue section analyzed, the area of interest may represent nearly the entire disc or only a small percentage thereof. For example, a pancreatic carcinoma or lobular carcinoma of the breast with substantial dysplastic response may show stromal tissue representing a large percentage of the total area of the disc. If the goal of the assay is to determine epithelial cell expression of a given marker, a protocol must be used that evaluates only that component of the disc. While specific examples are provided, it will be appreciated that any stain that selectively stains one or more features of diagnostic, structural, or other interest within a tissue microarray may be usefully employed with the systems herein. In general, the protocol may identify regions of interest and provide normalization operations so that the expression level read from any given disc can be compared with that of other discs. One suitable technique for image analysis employing color decomposition is described below.

As shown in step 412, images and image data, such as image location and the quantitative evaluations discussed above, may be archived. This may be performed automatically, with images and associated data being stored in one or more local and/or distributed relational databases. The commercially available Oracle 8i database system is one database suitable for use with the number and size of records typically encountered in the images contemplated herein. It will be appreciated that each of the steps of disc image acquisition 408, disc analysis 410, and data archiving 412 may be performed in parallel for all discs on a tissue microarray, for groups of discs such as rows, or individually for each disc, and repeated as appropriate until all discs on the tissue microarray are processed. The order in which discs are processed may depend on memory and processing constraints of the system employed, or upon programming convenience. In one embodiment, each disc is processed individually and fed to a database before the next disc in the tissue microarray is analyzed. One database architecture useful for storing image data is described in greater detail below.

Once data has been archived in step 412, data may be managed, as shown in step 414. It will be appreciated that this step may be performed immediately upon completion of step 412, or at some subsequent time at a user's convenience. The system may allow a user to design the data format for new tissue microarrays with options for labeling the discs individually or in groups. The interface may also allow for color coding of the elements (discs) from each subset and for arranging cases. Disc images, and the associated data (such as image metrics and protein expression levels) may be managed across a number of tissue microarrays and cohorts. Thus new, virtual tissue microarrays may be created from disparate sets of archived data, thereby facilitating the design of new experiments from ensembles of existing cases. Thus, a virtual microscope may be created for viewing a variety of tissue microarrays from any number of different physical tissue microarrays.

As shown in step 416, the process 400 may end, with a structured database of results available for review by clinicians and/or researchers at local or remote locations.

Figure 5:
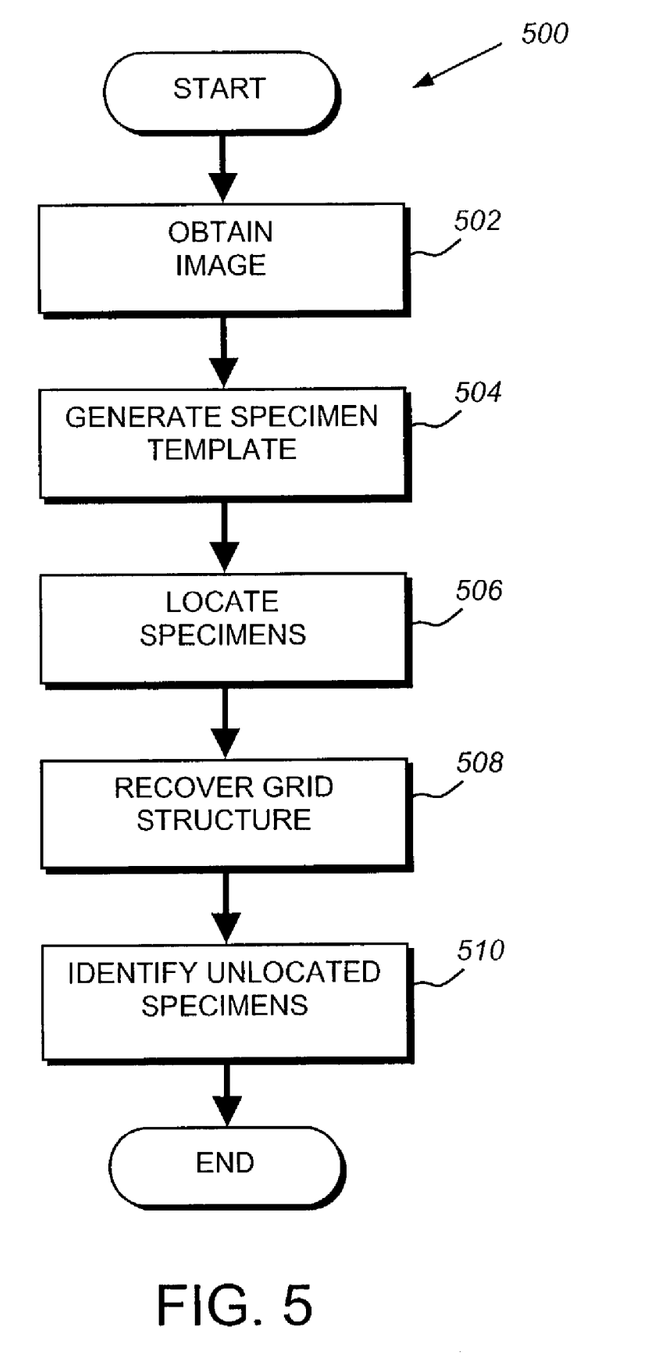
FIG. 5 is a flow chart depicting a technique for unsupervised registration of a microtissue array image.

FIG. 5 is a flow chart depicting a technique for unsupervised registration of a microtissue array image. Generally, a process 500 extracts grid locations for each disc within a tissue microarray. While it is possible to extract grid locations for a microarray using uncalibrated imaging hardware, a system preferably employs a calibrated imaging system so that subsequently obtained image data are more consistent across a number of different microarray images.

As shown in step 502, the process 500 begins by obtaining an image of an entire tissue microarray. A quilted digital version of the microarray may be automatically generated using slightly overlapping frames of adjacent optical fields. These adjacent fields may be combined into a composite image. Image quality may be maintained across optical field images using, for example, entropy-based auto-focusing.

As shown in step 504, the process 500 may generate a specimen template representative of specimens that are to be located in the composite image. Using, for example, the round discs typical of microtissue arrays, a known core diameter for each disc may be used, in combination with microscope magnification and scan settings to determine an expected size, in units such as pixels, of specimens in the composite image. The template may be formed by encoding a first value, typically a '1', into each pixel within a (expected) specimen image, and a second value, typically a '−1' for contrast, into a two-pixel boundary around the (expected) specimen image.

As shown in step 506, specimens may be located within the composite image by applying the template obtained in step 504 to the composite image obtained in step 502. This may be accomplished using, for example, a discrete convolution of the template with the composite image. A Mexican-hat operator (a combination of Gaussian smoothing and Laplacian zero-crossing functions commonly used, for example, in image processing operations such as edge detection or local feature detection) and spatial filtering may be used to ensure that the discrete convolution yields only one centroid point for each specimen.

As shown in step 508, the grid structure of x and y locations for discs in the tissue microarray may be recovered. While the locations of certain discs may be identified using the template described above, some disc locations within the tissue microarray may not match the template, such as when a disc has become dislodged, or when staining or other slide processing fails to produce visual characteristics corresponding to the template. In such cases, a location of the disc may nonetheless be identified by modeling the grid of discs in the microarray based upon those discs which are identified using the template. In general, a Hough transformation may be applied to identify the grid corresponding to the located specimens, as described in more detail below.

The grid structure of the microarray may be determined by detecting the centroids of candidate discs as described above and utilizing a modified Hough transformation to identify the underlying grid. One way to detect straight lines in Cartesian coordinate systems is to map candidate lines $y=tg(\theta)x+b$ from each pair of candidate points into $(\theta, b)$ in Hough space, as more fully described, for example, in "Image Processing Handbook, $2^{nd}$ Ed.", J. C. Ross (CRC Press, 1995). Utilizing two-dimensional peak detection algorithms, it is then possible to identify points which exhibit local maximums corresponding to lines in the original image. Due to the grid-like arrangement of tissue microarrays, when the resulting Hough space is projected onto the θ axis, there are two peaks detected which are 90° from one another. These peaks corresponded to the column and row orientation, i.e., the overall grid of the array. The intercepts may then be computed by least-square fitting. By this process, the two-dimensional peak detection process may be simplified into two, one-dimensional operations to reduce computation.

Figure 6:
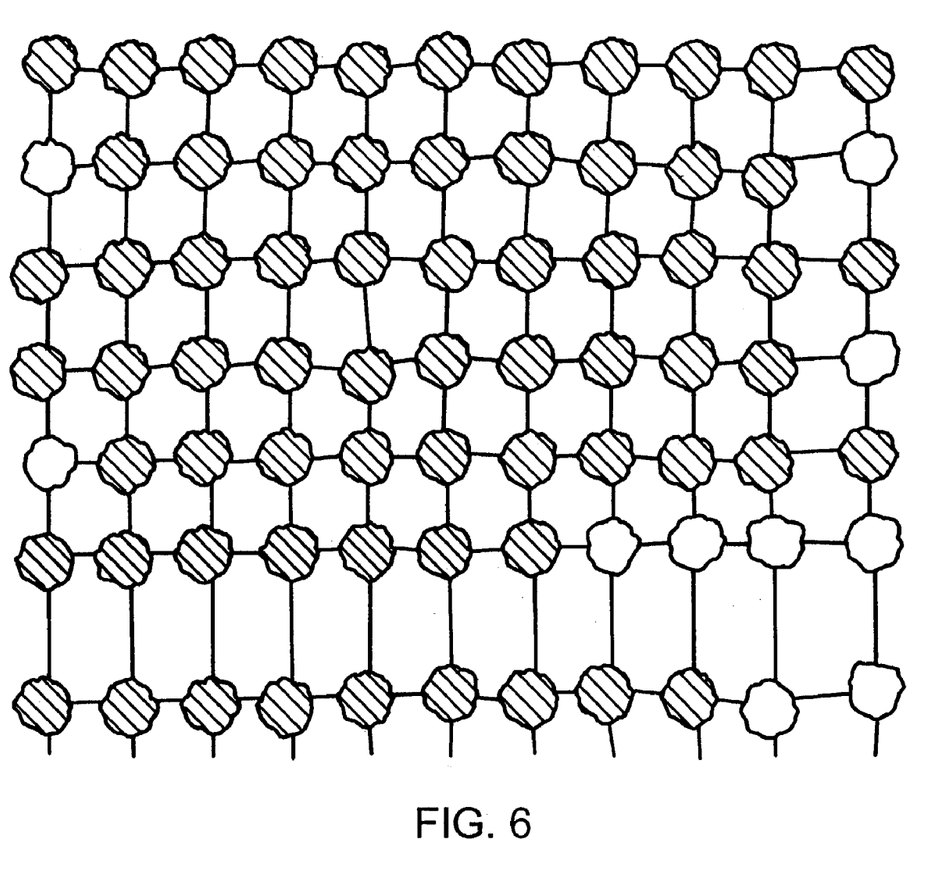
FIG. 6 depicts a recovered grid of a tissue microarray as it might be displayed on a user interface.

As shown in step 510, the grid may be used to identify specimens that were not located through application of the template to the composite image. An example of a recovered grid is depicted in FIG. 6, as it might be displayed on a user interface of a client device. It will be noted that the grid includes discs that were identified using the template, which are shaded, and discs which were identified using the grid, which are not shaded.

Other techniques for locating shapes are known, and may be usefully employed with the systems and methods described herein. However, the above described approach has empirically proven well-suited to use with discs in a tissue microarray. For example, the grid recovery technique is particularly well-suited to identifying disc locations, whether or not positively stained, within a physically malleable tissue microarray where the grid may be deformed during handling. It will be appreciated that modifications will be appropriate for other arrays that are not arranged into a rectangular matrix of disc-shaped samples having regular rows and columns. Once disc images have been located within a composite image, each disc image may be processed and analyzed to extract information from the disc's visual content.

Figure 7:
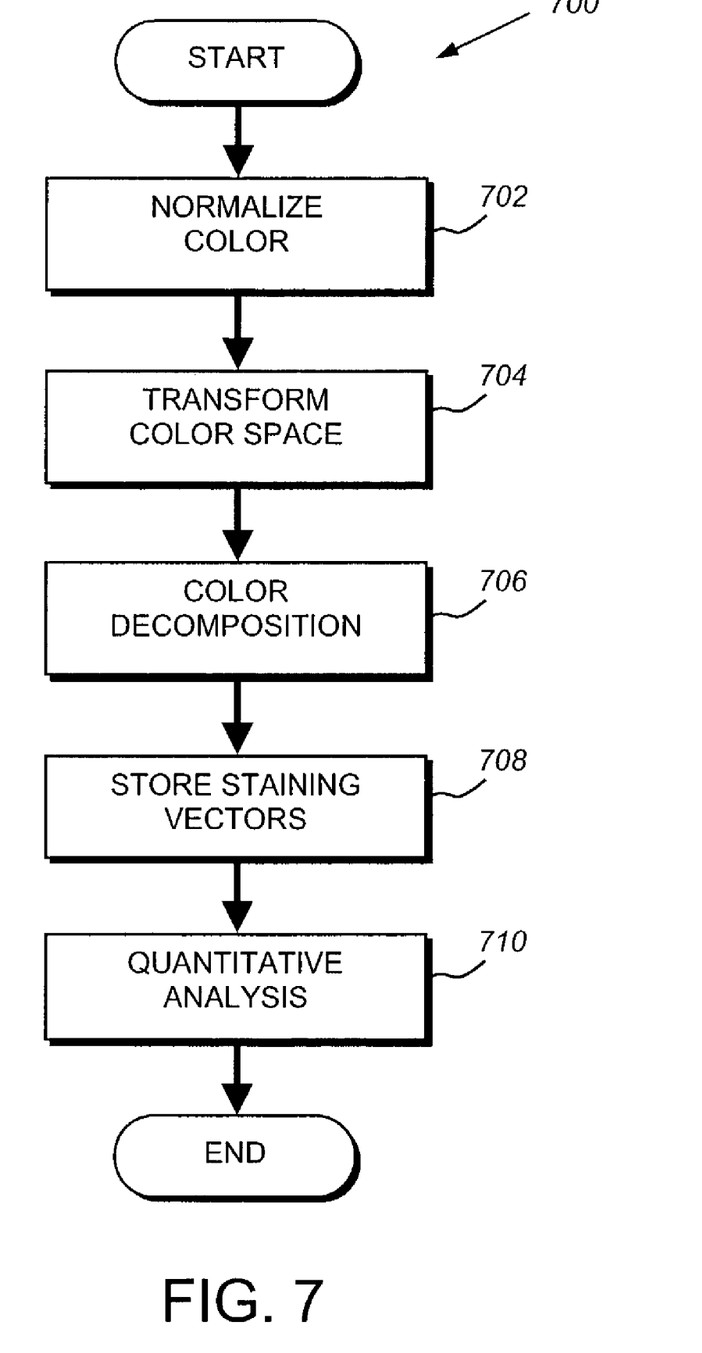
FIG. 7 is a flow chart depicting a process for analyzing disc images.

FIG. 7 is a flow chart of a process for analyzing disc images. When only a single stain is used to prepare a specimen, staining intensity may be determined from the integrated pixel density, i.e. luminance, on the corresponding disc image. This, in turn, relates to the amount of specific antigen molecules or binding sites. However, in most cases, two or more dyes are used with one acting as the counter stain which serves to reveal the histological context of the specimen. Since each of the colors within the specimen can contribute to the luminance of the image, proper color separation should be performed before using a luminance measurement as an indication of staining intensity.

A color separation algorithm may be applied to detect and characterize staining characteristics within a tissue mircoarray having multiple stains, as described in greater detail below. In an embodiment, the techniques have been applied to tissue microarray specimens stained with DAB chromogen and counter-stained with hematoxylin, resulting in various shades and combinations of the two dye colors.

As shown in step 702, the process 700 may begin by normalizing color vectors. Using, for example, RGB color data captured by the hardware described above, an average background color may be calculated for an entire array of specimens. This color value may then be subtracted from the RGB color vector for each pixel to produce background-corrected values for that pixel. Any pixel which has an adjusted RGB value which falls outside of the 0–255 range may be assigned the white value of 255.

As shown in step 704, the color space may then be transformed into a polar representation. Depending on the original data format, this may involve a single transformation from the conventional L*u*v* color space into a polar representation of same, L*$h_{uv}$*$C_{uv}$*, or it may include a preliminary transformation from another color space, such as Red-Green-Blue ("RGB") or Cyan-Magenta-Yellow ("CMY") into L*u*v*. These transformations may be performed, for example, on a pixel-by-pixel basis to each disc image. The transformation to a polar representation may be performed using the following mapping:

$$h_{uv}^* = \arctan\left(\frac{v^*}{u^*}\right), \text{ and} \quad \text{[Eq. 1]}$$

$$C_{uv}^* = \sqrt{(u^*)^2 + (v^*)^2}$$

Figure 8:
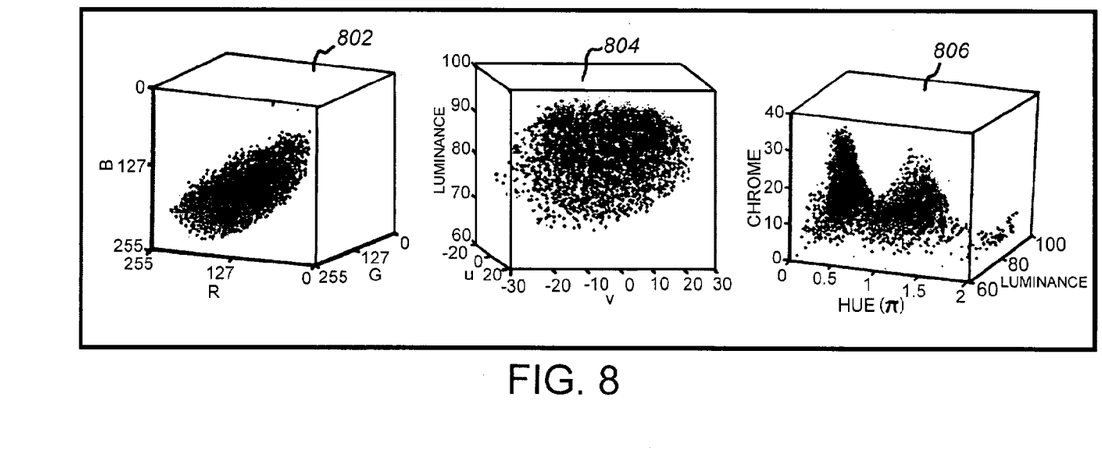
FIG. 8 shows three representations of an illustrative tissue microarray image dataset.

FIG. 8 shows three representations of an exemplary tissue microarray image dataset. The first representation 802 depicts the dataset in RGB space. The second representation 804 depicts the dataset in L*u*v* space. The third representation 806 depicts the polar transformation of the second representation 804, as mapped according to Eq. 1 above. In the third representation 806, two color peaks are clearly visible. These peaks correspond to the color vectors for the specimen stains. A number of peak values, such as twenty, for each peak may be averaged to obtain principal color vectors for the two stains. Other techniques, such as regression analysis, may be similarly employed to recover peak values corresponding to the principal color vectors in this color space.

Returning to FIG. 7, color decomposition may be performed as shown in step 706. Principal color vectors in L*u*v* space may be determined using the techniques above. The principal color vectors may be corrected based upon absolute white using L'=100−L. A third, orthogonal vector, for use in decomposition of a three-dimensional color vector, may be identified with a cross-product of the two known vectors:

$$C_3 = C_1 \otimes C_2 = \begin{vmatrix} L' & u & v \\ L'_1 & u_1 & v_1 \\ L'_2 & u_2 & v_2 \end{vmatrix} \quad \text{[Eq. 2]}$$

Each adjusted RGB color, as described above with reference to step 702, may be decomposed into:

$$C = \alpha C_1 + \beta C_2 + \gamma C_3 \quad \text{[Eq.3]}$$

By solving:

$$\begin{bmatrix} L' \\ u \\ v \end{bmatrix} = \begin{bmatrix} L'_1 & L'_2 & L'_3 \\ u_1 & u_2 & u_3 \\ v_1 & v_2 & v_3 \end{bmatrix} \times \begin{bmatrix} \alpha \\ \beta \\ \gamma \end{bmatrix} \quad \text{[Eq. 4]}$$

The γ value has empirically been determined to be negligible for the dual-stained tissue microarrays described above. The resulting vector:

$$\begin{bmatrix} \alpha \\ \beta \end{bmatrix}$$

for any original RGB color vector corresponds to the staining signatures of the two dyes at that pixel location.

As shown in step 708, each resulting vector obtained in step 706 for a pixel location may be indexed into a data structure along with the original RGB color vector for that pixel location. The vector, which we refer to herein as the staining vector, corresponds to the staining signatures of the two dyes for that location, and may be used for subsequent visualization or analysis of a specimen from the tissue microarray. The staining vectors may be used to assist in further quantitative or qualitative analysis. Quantitative analysis is described in further detail below, Qualitative analysis may be facilitated by, for example, generating an image that depicts staining intensity for only one out of two dyes used to stain a tissue microarray, superimposed on an image of one of the specimens. An example of applied color decomposition for a tissue microarray stained with DAB and hematoxylin is provided in FIG. 9, which shows an RGB image alongside dye maps obtained through color decomposition as described above.

Figure 9A:
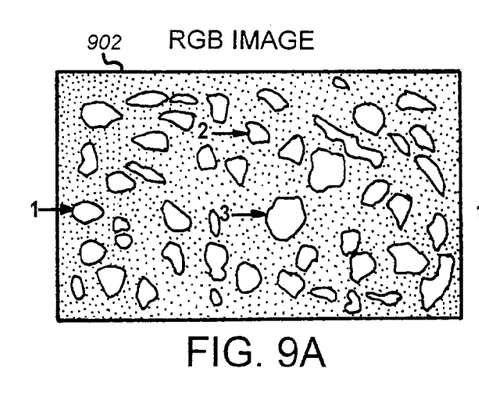
FIGS. 9A–9C show an RGB image alongside dye maps obtained through color decomposition.
Figure 9B:
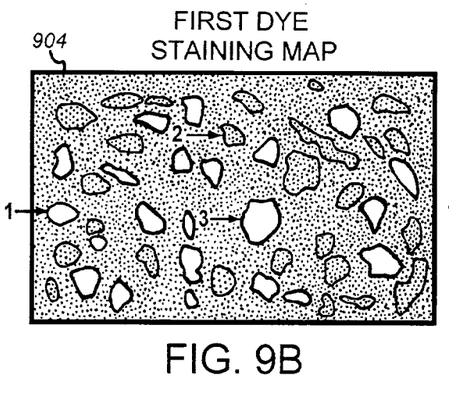
Figure 9C:
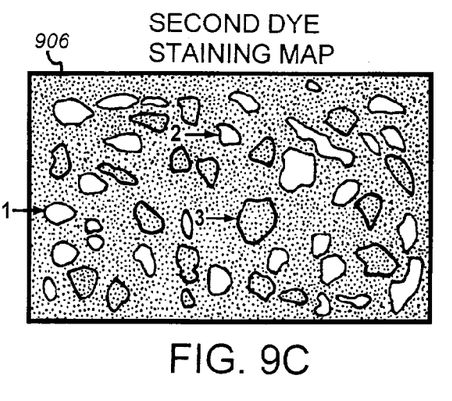

FIGS. 9A–9C show an RGB image alongside dye maps obtained through color decomposition. It should be appreciated that these figures present a highly stylized rendering of a microscope image intended to illustrate visual differentiation of stained subject matter. While similar in overall appearance to images obtained from a tissue microarray, these figures should not be interpreted as literal reproductions of such microscope images. FIG. 9A depicts an RGB image 902 of a disc from a tissue microarray. FIG. 9B shows intensity for a first staining map 904 showing greater intensity (white) for areas stained with DAB. FIG. 9C shows intensity for a second staining map 906 showing greater intensity for areas stained with hematoxylin. It will be noted generally that structures within the image may be stained by one or the other of the two dyes, or in certain cases, by both dyes, this latter case corresponding to structures having high intensity in the first and second staining maps 904, 906. For example, it will be noted that certain structures 1, 2, 3 visible in the RGB image 902 may be visible in the first staining map 904 (e.g., structure 3), the second staining map 906 (e.g., structure 2), or both (e.g., structure 1).

Returning now to FIG. 7, and more particularly to step 710, any quantitative analysis may be performed on the resulting dataset. In a feasibility study using the hardware described above, color vectors that were generated for a representative tissue microarray that had been stained with DAB and hematoxylin. A dataset of one-hundred forty specimens, each having 1368×1232 pixels, resulted in 500,000 RGB color vectors, which were transformed into a polar $L^*h_{uv}C_{uv}$. Two principal peak colors were identified as principal color vectors of stain signatures for each of the two dyes. All colors were then decomposed according to the two principal color vectors and a third, orthogonal vector. Using a conventional desktop computer, this entire procedure has been completed in a few seconds. The techniques described above unveiled and quantified the underlying staining characteristics all specimens, even those cells with visual masking due to the counterstain.

More generally, by projecting color data onto two principal color vectors associated with stains, a separation of staining intensity for each dye was reliably obtained. As a significant advantage, the analysis on dual-stained specimens may be completed with substantially reduced computational complexity as compared to other color analysis techniques known in the art.

An integrated staining intensity may be calculated as the sum of DAB staining intensity over an entire disc. An effective staining area may be calculated as a proportion of pixels which express above a user-specified threshold. An effective staining intensity may be calculated as an average staining intensity divided by the effectively stained pixels. Discs having an effective staining area below some threshold, e.g., 1000 pixels out of 4,000 or more, as non-stained. These discs may be assigned a zero effective staining intensity automatically. Other quantitative analyses may be devised and useful employed with the data derived from the techniques described above.

Figure 10:
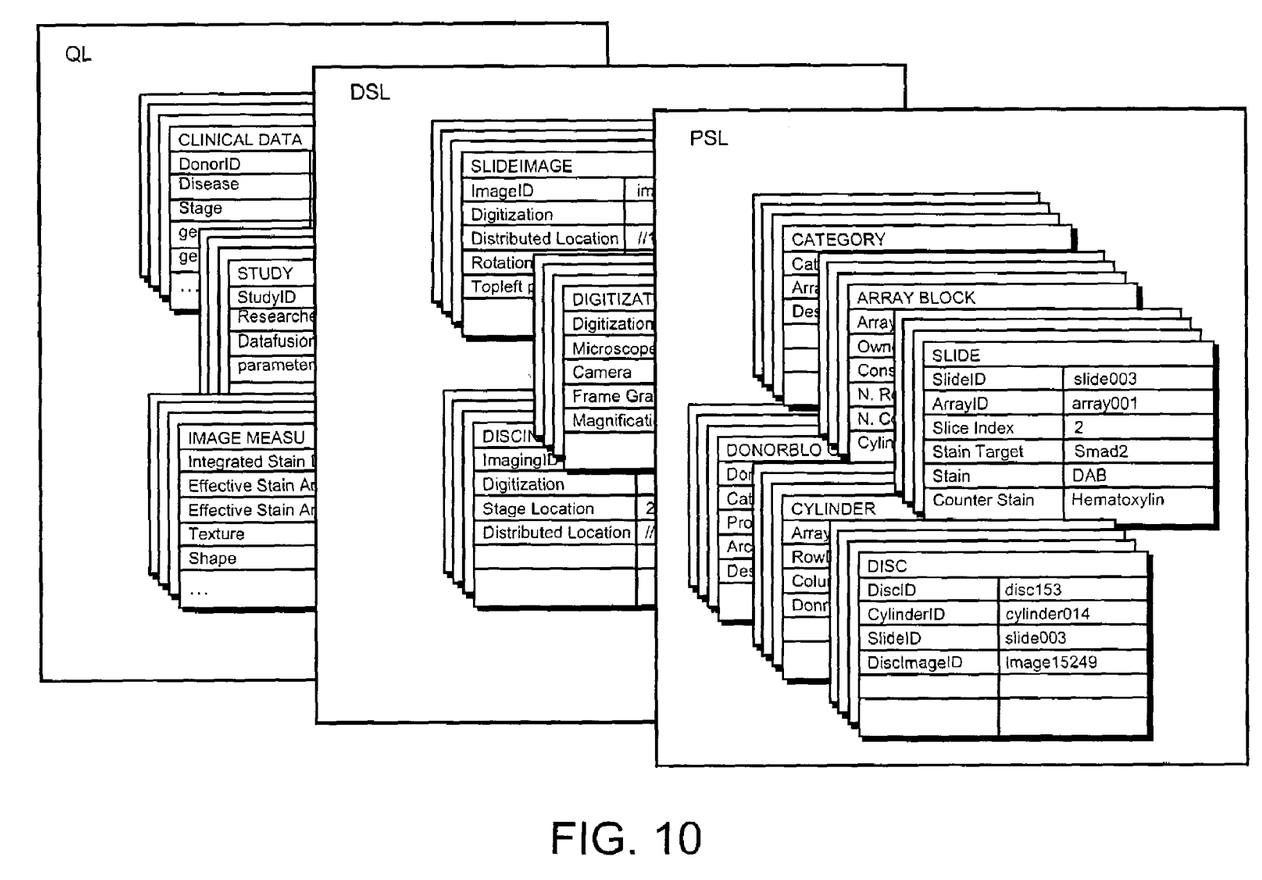
FIG. 10 depicts a data structure that may be employed to store tissue microarray data.

FIG. 10 depicts a data structure that may be employed to store tissue microarray data. The data structure may be created in, for example, an Oracle8i database, and used to store tissue microarray data obtained through the systems and methods described above. While the structure is in many aspects only illustrative, it will be noted that data is organized into a physical specimen layer ("PSL"), a digital sample layer ("DSL"), and a quantification layer ("QL"). An interface may be provided to adapt data structures to particular microarrays and donor information.

The physical specimen layer may relate to physical properties and preparation of the tissue microarray sample, including, for example, an array format (dimensions, shape, interval of samples), donor block information describing donors and physical characteristics or pathology data of donors, and array construction data that relates grid locations to particular donors.

The digital sample layer (DSL) of the database may store pointers to the archived digital images and image maps as well as the corresponding images of each tissue disc at multiple resolutions. High-resolution images of tissue discs may be stored on a computer disc or other mass storage device with a pointer stored in the database to indicate its location(s) along with all scanning settings.

Since tissue microarray techniques result in a standardized set of tissue samples, they may provide a useful dataset for developing and evaluating image processing and computer vision protocols, which can be used to perform quantitative immuno-histochemistry. The third layer of the database, the quantification layer (QL), supports automated segmentation and computation of protein expression levels across each disc as described above, as well as storage of any other quantitative data derived from tissue microarray images.

It will be appreciated that the above process is merely illustrative, and that other steps and procedures, or system features, may be usefully deployed with a system as described herein, in addition to, or instead of, those disclosed herein. For example, missing discs may be located through direct inspection of the convolution results, and in certain circumstances, calibration may be omitted.

In one embodiment, the steps of the process 400 are performed by a computer locally connected to a robotic microscope. In another embodiment, the steps of the process 400 are performed by a computer that communicates with the robotic microscope through an internetwork. In either embodiment, access to the image archives may be provided to remote clients through the internetwork. A voice-activated user interface may be provided to simplify computer control over the archiving process, or over review of archived data.

Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the following claims should be interpreted in the broadest sense allowable by law.

What is claimed is:

1. A method comprising:
staining a tissue microarray with a first stain and a second stain to obtain a stained tissue microarray, each of the first stain and the second stain selectively staining portions of the tissue microarray;
capturing an image of the stained tissue microarray, the image including a plurality of specimen images;
analyzing the image to identify a first color vector corresponding to the first stain and a second color vector corresponding to the second stain; and
measuring a presence of each one of the first color vector and the second color vector in one or more of the plurality of specimen images.

2. The method of claim 1 wherein the image comprises a plurality of digital images captured by an imaging device and combined into a composite image of the stained tissue microarray.

3. The method of claim 1 wherein capturing an image further comprises capturing an image with a robotic microscope.

4. The method of claim 1 wherein one of the first stain or the second stain is a histochemical stain.

5. The method of claim 1 wherein one of the first stain or the second stain is an immunologic stain.

6. The method of claim 1 wherein one of the first stain or the second stain selectively stains one or more features of diagnostic interest.

7. The method of claim 1 wherein analyzing the digital image further comprises transforming image data into a polar coordinate space and identifying peak color vectors within the polar coordinate space.

8. The method of claim 1 further comprising displaying one of the plurality of specimen images and a selected one of the first stain or the second stain.

9. The method of claim 1 wherein measuring a presence of each one of the first color vector and the second color vector in one of the plurality of specimen images comprises comparing the first color vector and the second color vector to the one of the plurality of specimen images on a pixel-by-pixel basis, thereby providing a staining vector for each pixel of the specimen image.

10. A computer program embodied in a computer readable medium comprising:
computer executable code for capturing an image of a stained tissue microarray stained with a first stain and a second stain, the image including a plurality of specimen images;
computer executable code for analyzing the image to identify a first color vector corresponding to the first stain and a second color vector corresponding to the second stain; and
computer executable code for measuring a presence of each one of the first color vector and the second color vector in one or more of the plurality of specimen images.

11. A system comprising:
staining means for staining a tissue microarray with a first stain and a second stain to obtain a stained tissue microarray, each of the first stain and the second stain selectively staining portions of the tissue microarray;
imaging means for capturing an image of the stained tissue microarray, the image including a plurality of specimen images;
first computing means for analyzing the image to identify a first color vector corresponding to the first stain and a second color vector corresponding to the second stain; and
second computing means for measuring a presence of each one of the first color vector and the second color vector in one or more of the plurality of specimen images.

12. A system comprising an imaging device and a computer, the imaging device responsive to a control signal to provide images at a specified magnification and a specified location within a tissue microarray, and the computer providing the control signal to the imaging device and receiving the images provided by the imaging device, the computer configured to analyze images of the tissue microarray to identify one or more color vectors associated with one or more dyes used to stain the tissue microarray, the computer further configured to capture a specimen image of each one of one or more specimens within the tissue microarray and to measure a presence of each one of the one or more color vectors within each specimen image.

13. The system of claim 12 wherein the imaging device includes a robotic microscope.

14. The system of claim 12 wherein the imaging device includes a virtual microscope.

15. The system of claim 12 wherein the imaging device is further responsive to a control signal received through a connection to a network, the imaging device being controlled from a remote location through a web-based interface.

16. The system of claim 12 wherein the system identifies the color vector associated with each of the one or more dyes by transforming digital image data from the images of the tissue microarray into a polar coordinate space and analyzing the transformed digital image data to identify a peak.

17. The system of claim 12 further comprising a database for storing in a structured form digital image data from the tissue microarray, data concerning physical properties and preparation of the tissue microarray, and data derived from the digital image data.

18. The system of claim 12 wherein the computer is further configured to generate a processed image that includes on of the specimen images and, superimposed on the specimen image, a selected one of the dyes used to stain the tissue microarray.

19. The system of claim 18 further comprising a display connected to the computer and displaying the processed image.

20. The system of claim 12 wherein the one or more dyes used to stain the tissue microarray selectively stain one or more features of diagnostic interest.

21. A method comprising:
staining a tissue microarray with a first stain and a second stain to obtain a stained tissue microarray, each of the first stain and the second stain selectively staining portions of the tissue microarray;
capturing an image of the stained tissue microarray, the stained tissue microarray including a plurality of discs, each disc including a sample of a biological specimen;
locating a first group of discs from the plurality of discs using one or more visual features of the first group of discs;

identifying a grid defined by the first group of discs;

locating a second group of discs from the plurality of discs using the grid to locate discs which do not include the one or more visual features of the first group of discs;

capturing a specimen image of each one of the first group of discs and the second group of discs to provide a plurality of specimen images;

analyzing the image of the stained tissue microarray to identify a first color vector corresponding to the first stain and a second color vector corresponding to the second stain; and measuring a presence of each one of the first color vector and the second color vector in one or more of the plurality of specimen images.

* * * * *